(12) United States Patent
Shoureshi

(10) Patent No.: US 7,437,934 B2
(45) Date of Patent: Oct. 21, 2008

(54) SELF-CONTAINED APPARATUS FOR INSPECTION OF ELECTRIC CONDUCTORS

(76) Inventor: Rahmat A. Shoureshi, 1992 Montane Dr. East, Golden, CO (US) 80401

( * ) Notice: Subject to any disclaimer, the term of this patent is extended or adjusted under 35 U.S.C. 154(b) by 40 days.

(21) Appl. No.: 11/549,213

(22) Filed: Oct. 13, 2006

(65) Prior Publication Data

US 2008/0087091 A1 Apr. 17, 2008

(51) Int. Cl.
*G01N 29/04* (2006.01)
*G01R 31/11* (2006.01)
(52) U.S. Cl. .......................... 73/643; 324/543
(58) Field of Classification Search ............... 73/643; 324/543
See application file for complete search history.

(56) References Cited

U.S. PATENT DOCUMENTS 4,829,298 A * 5/1989 Fernandes .............. 340/870.27
5,565,783 A * 10/1996 Lau et al. .................... 324/522
6,382,029 B1   5/2002 Shoureshi et al.

* cited by examiner

*Primary Examiner*—John E Chapman
(74) *Attorney, Agent, or Firm*—Trego, Hines & Ladenheim, PLLC

(57) ABSTRACT

A self-contained apparatus for inspecting energized and de-energized conductors. The apparatus includes a housing, at least one transmitter contained within the housing for generating and impinging pulses onto an electrical conductor, such that the pulses travel through and are reflected by the electrical conductor, and at least one receiver contained within the housing for receiving reflected pulses from the electrical conductor. The apparatus further including a controller for determining a condition of the electrical conductor based on an evaluation of the reflected pulses, and at least one indicator for displaying the condition of the electrical conductor determined by the controller.

34 Claims, 19 Drawing Sheets

SELF-CONTAINED APPARATUS FOR INSPECTION OF ELECTRIC CONDUCTORS

TECHNICAL FIELD AND BACKGROUND OF THE INVENTION

The present invention relates to the field of electric conductor inspection. In particular, the invention relates to a self-contained apparatus for inspecting energized and de-energized conductors.

Utility companies have long sought to reap the benefits of early detection of overhead power line/conductor defects. Identifying conductor issues early can facilitate the maintenance and replacement decision making process and prioritize repairs that should be made. Correctly separating troubled conductors from those with additional life can help companies avoid expensive maintenance work, line-drops, failures, and regional outages.

A number of methods and technologies have been used to detect damaged or aged transmission conductors. These include visual inspection, infrared thermography, and overhead line corrosion detection (OHLCD).

The traditional method for detecting damage to an overhead transmission conductor has required power company line personnel to disassemble and remove tower hardware and armor rods and open up the conductor for visual inspection. This "hands on" method of inspection requires the conductor to be de-energized in most cases. Further, line personnel are only able to detect damage to the outer strands of the conductor and cannot see critical sub-surface damage.

OHLCD technology uses a trolley unit that contains both a corrosion detector and a data telemetry system. The unit is attached to the conductor in question and towed along the conductor by a second lightweight, motorized radio-controlled trolley. While this technology is able to detect corrosion in the conductor core, it does not look at the effects of corrosion on the outer conductor strands. Also, the unit is not capable of testing areas under suspension clamps unless they are removed, thus, requiring the conductor to be de-energized. Further, OHLCD technology does not detect strand breaks or non-functional splice repairs.

Infrared thermography and X-ray techniques have improved the ability of utility companies to detect issues with substation and tower hardware. However, these techniques have been less successful at the detection of flaws in overhead transmission conductors. Infrared or X-ray surveys of transmission conductors require an airplane and other expensive equipment. The costs of such services and the limited results they yield have yet to demonstrate a real cost-benefit justification.

The high-cost and time-intensive nature of the methods described above coupled with tight operational and maintenance budgets have resulted in infrequent conductor inspection and a growing risk of failure that is neither quantified nor fully understood. As a result, companies are forced to make decisions regarding the replacement of power transmission conductors without proper diagnosis tools. These decisions often result in the replacement of conductors with remaining life and the non-replacement of conductors near failure, thereby resulting in substantial costs per year for unneeded replacements. Armed with solid information about the relative condition of various transmission conductors, utility personnel can make more effective operational and maintenance decisions that save the company substantial amounts of both time and money.

Accordingly, there is a need for a self-contained apparatus that allows companies to test conductors accurately and efficiently for corrosion, poorly installed splices, and broken strands of the conductors without de-energizing the conductors or disassembling hardware.

SUMMARY OF THE INVENTION

Therefore it is an object of the invention to provide a self-contained apparatus that can detect small flaws in a conductor quickly and efficiently, whether the conductor is energized or de-energized.

It is another object of the invention to provide a self-contained apparatus that provides non-invasive inspection of a conductor.

It is another object of the invention to provide a self-contained apparatus that can detect subsurface damage of a conductor.

It is another object of the invention to provide a self-contained apparatus that can detect corrosion on a conductor's surface and it's core.

It is another object of the invention to provide a self-contained apparatus that is portable and can be quickly attached and detached from a conductor.

It is another object of the invention to provide a self-contained apparatus that can test conductors of various sizes.

These and other objects of the present invention are achieved in the preferred embodiments disclosed below by providing an apparatus for inspecting electrical conductors including a housing; at least one transmitter contained within the housing for generating and impinging pulses onto an electrical conductor, such that the pulses travel through and are reflected by the electrical conductor; and at least one receiver contained within the housing for receiving reflected pulses from the electrical conductor. The apparatus further including a controller for determining a condition of the electrical conductor based on an evaluation of the reflected pulses; and at least one indicator for displaying the condition of the electrical conductor determined by the controller.

According to another preferred embodiment of the invention, the housing includes an upper housing portion and a lower housing portion.

According to another preferred embodiment of the invention, the upper housing portion and lower housing portion are moveable relative to each other from an open position for receiving the electrical conductor to a closed position for inspecting the electrical conductor.

According to another preferred embodiment of the invention, the at least one transmitter and at least one receiver form an electromagnetic acoustic transducer system.

According to another preferred embodiment of the invention, the controller includes an on-board microprocessor for evaluating the condition of the electrical conductor.

According to another preferred embodiment of the invention, the microprocessor uses software selected from the group consisting of fuzzy logic, neural network, and adaptive resonant theory network to provide system operation, fault detection, and classification of the condition of the electrical conductor.

According to another preferred embodiment of the invention, the housing portion includes an attachment device for attaching a hot stick thereto to allow the apparatus to be positioned on energized electrical conductors.

According to another preferred embodiment of the invention, a bounding fork is connected to the housing to discharge any electrical charge that could damage the apparatus when placing the apparatus on an energized electrical conductor.

According to another preferred embodiment of the invention, and further including a motor drive assembly for moving the upper housing portion and lower housing portion relative to each other from an open position where the electrical conductor is received therebetween to a closed position where the electrical conductor is clamped therebetween for testing.

According to another preferred embodiment of the invention, the motor drive assembly includes a feedback controlled motor and a gear drive.

According to another preferred embodiment of the invention, and further including screw guides operably connected to the gear drive and feedback controlled motor to allow the upper housing portion and lower housing portion to be moved from the open position to the closed position.

According to another preferred embodiment of the invention, the housing is curve-shaped to prevent corona and made of a material capable of withstanding at least 500 kV and at least 1000 amperes.

According to another preferred embodiment of the invention, and further including a plurality of switches positioned on the housing for manually controlling the apparatus.

According to another preferred embodiment of the invention, the upper housing portion and lower housing portion each include a recess for receiving a transmitter/receiver cartridge therein.

According to another preferred embodiment of the invention, each of the transmitter/receiver cartridges is operably connected to the at least one transmitter and the at least one receiver.

According to another preferred embodiment of the invention, each of the transmitter/receiver cartridges is removable and can be interchanged with other transmitter/receiver cartridges for testing on various sized electrical conductors.

According to another preferred embodiment of the invention, each of the transmitter/receiver cartridges includes both a transmitter coil and a receiver coil.

According to another preferred embodiment of the invention, the transmitter coil and receiver coil for each of the transmitter/receiver cartridges are connected in series.

According to another preferred embodiment of the invention, the at least one transmitter includes a pulse generator for creating electric pulses having a frequency between about 50 KHz and about 200 KHz.

According to another preferred embodiment of the invention, the at least one transmitter includes a high voltage generator for creating high voltage electric pulses.

According to another preferred embodiment of the invention, the at least one transmitter includes a clocks and power on reset generator for initiating the creation of pulses in response to actuation of a test switch positioned on the housing.

According to another preferred embodiment of the invention, the at least one receiver includes a signal amplifier for amplifying current induced by reflective displacement waves of the conductor.

According to another preferred embodiment of the invention, the at least one receiver includes a negative voltage generator to stabilize an output voltage and reduce noise.

According to another preferred embodiment of the invention, a self-contained electromagnetic acoustic transducer system for inspecting energized and de-energized electrical conductors includes a first transmitter/receiver cartridge releasably secured in a recess of an upper housing portion of a housing and a second transmitter/receiver cartridge releasably secured in a recess of a lower housing portion of the housing, the upper housing portion and lower housing portion being operably attached to each other for movement between an open position for receiving an electrical conductor between the first and second transmitter/receiver cartridges and a closed position where the electrical conductor is clamped between the first and second transmitter/receiver cartridges for testing. The system further includes at least one transmitter operably connected to the first and second transmitter/receiver cartridges for generating and impinging pulses onto the electrical conductor, wherein the pulses travel through and are reflected by the electrical conductor; at least one receiver operably connected to the first and second transmitter/receiver cartridges for receiving reflected pulses from the electrical conductor; a controller for determining a condition of the electrical conductor based on an evaluation of the reflected pulses; and a plurality of indicators for displaying the condition of the electrical conductor determined by the controller.

According to another preferred embodiment of the invention, the first and second transmitter/receiver cartridges are removable and can be interchanged with other transmitter/receiver cartridges for testing on various sized electrical conductors.

According to another preferred embodiment of the invention, the first and second transmitter/receiver cartridges each include a transmitter coil and a receiver coil.

According to another preferred embodiment of the invention, the transmitter coil and receiver coil for each of the first and second transmitter/receiver cartridges are connected in series and appear as a single transmitter coil or receiver coil to the system.

According to another preferred embodiment of the invention, the at least one transmitter includes a pulse generator for creating electric pulses having a frequency between about 50 KHz and about 200 KHz; a high voltage generator for creating high voltage electric pulses; and a clocks and power on reset generator for initiating the creation of pulses in response to actuation of a test switch.

According to another preferred embodiment of the invention, the at least one receiver includes a signal amplifier for amplifying current induced by reflective displacement waves of the conductor, and a negative voltage generator to stabilize an output voltage and reduce noise.

According to another preferred embodiment of the invention, and further including a motor driver for controlling the motor drive assembly.

According to another preferred embodiment of the invention, a method for inspecting an electrical conductor includes the steps of providing an apparatus that includes an upper housing portion movably connected to a lower housing portion; at least one transmitter; at least one receiver; and at least one controller; and placing the apparatus on an electrical conductor such that the electrical conductor is positioned between the upper housing portion and the lower housing portion. The method further including the steps of transmitting a signal through the electrical conductor using the at least one transmitter; capturing a reflection of the amplified signal with the at least one receiver; processing and filtering the reflection of the amplified signal in the controller; and providing an indication of a condition of the electrical conductor based on the processed and filtered reflection of the amplified signal.

According to another preferred embodiment of the invention, and further including the step of attaching one or more hot sticks to an attachment device on the upper housing portion.

According to another preferred embodiment of the invention, and further including the step of positioning a first transmitter/receiver cartridge in a recess of the upper housing portion and a second transmitter/receiver cartridge in a recess of the lower housing portion, wherein the first and second transmitter/receiver cartridges are sized for the electrical conductor.

According to another preferred embodiment of the invention, and further including the step of moving the upper housing portion and lower housing portion to an open position for receiving the electrical conductor.

According to another preferred embodiment of the invention, and further including the step of moving the upper housing portion and lower housing portion to a closed position for clamping the electrical conductor between the first and second transmitter/receiver cartridges.

According to another preferred embodiment of the invention, the step of processing and filtering the reflection of the amplified signal includes the steps of obtaining ASCII coded frequency sweep data files; making data sets mean zeroed; and applying a high order band-pass filter. The step of processing and filtering further includes the steps of overlapping data files on a time domain; extracting the maximum value from each band-pass filtered data and constructing one time domain data file; strategically removing initial data points and final data points; applying a running average filter; and re-sampling of the data.

BRIEF DESCRIPTION OF THE DRAWINGS

The invention may be best understood by reference to the following description in conjunction with the accompanying drawing figures in which.

DESCRIPTION OF THE PREFERRED
EMBODIMENT AND REST MODE

Figure 1:
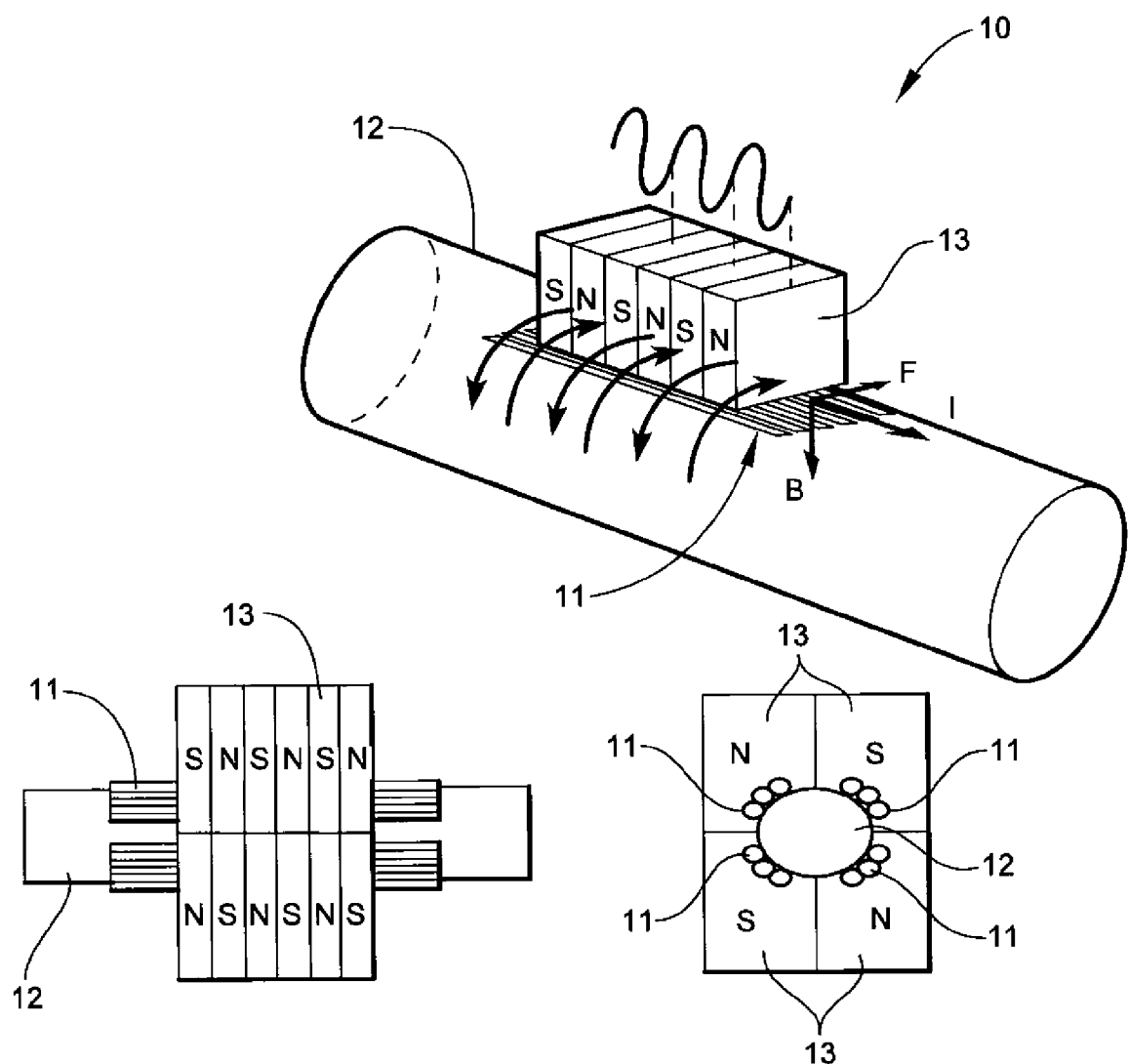
FIG. 1 shows a basic electromagnetic acoustic transducer (EMAT) setup.

Referring to FIG. 1, the present invention utilizes Electromagnetic Acoustic Transducers (EMAT) to monitor, diagnose, and identify failures in an energized or de-energized conductor, i.e. transmission lines. An EMAT 10 consists of a transmitter and a receiver. The EMAT 10 couples ultrasonic energy into conductive materials. The simplest form of an EMAT 10 is a wire loop held near a conductive material with a magnet placed above the wire. The transmitter operates based on principles similar to an electric motor, which develops torsional waves. As shown, a copper coil 11 is placed as close to a test specimen 12 as possible and an alternating current is injected. This current produces a dynamic magnetic field (H), which varies in time and space. The resulting eddy current density (J) produced in the test specimen 12 is given by Maxwell's equation, represented by:

$$\vec{J} = \vec{\nabla} \times \vec{H} \tag{1}$$

From Maxwell's equations for quasi-static conditions, this eddy current flows in the test specimen 12. To create a force in the test specimen 12, permanent magnets 13 with high intensity are placed directly over the coil 11 to immerse the test specimen 12 with magnetic flux. The eddy current interacts with the external magnetic flux density (B), to produce a force density given by:

$$\vec{F} = \vec{J} \times \vec{B} \tag{2}$$

Coupled to the lattice of the test specimen 12, this force is called a Lorentz force and acts in a direction, as indicated in FIG. 1. An elastic disturbance involving particle displacements (u) and velocity (du/dt) propagates through the test specimen 12. The receiver of the EMAT 10 works similar to an electric generator. When the elastic waves pass under the receiver, the surface of the specimen 12 is displaced in the magnetic field. Because of the resultant elastic displacement of the test specimen 12, an electric field (E) arises according to the following equation:

$$\vec{E} = \frac{d\vec{u}_{tot}}{dt} \times \vec{B} \tag{3}$$

where $du_{tot}/dt$ is the total particle velocity, which incorporates reflected, as well as incident elastic waves at the surface. With the resulting conduction current density, a related magnetic field ($H_R$) and the resulting electric field (E) for a sinusoidal time variations would be generated as described below:

$$\vec{H}_R = \left(\frac{1}{\mu_o}\right)(\vec{\nabla} \times \vec{A}) \tag{4}$$

$$\vec{E} = j\omega\vec{A} \tag{5}$$

where, A is the vector electric potential outside the test specimen 12 and around the receiver coil 11, $\mu_o$ is the permeability of free space, and $\omega$ is the frequency of the alternating current.

A further explanation of electromagnetic acoustic transducers and scientific principles related to analyzing in-service conductive materials is described in U.S. Pat. No. 6,382,029, issued to Shoureshi et al.

Figure 2:
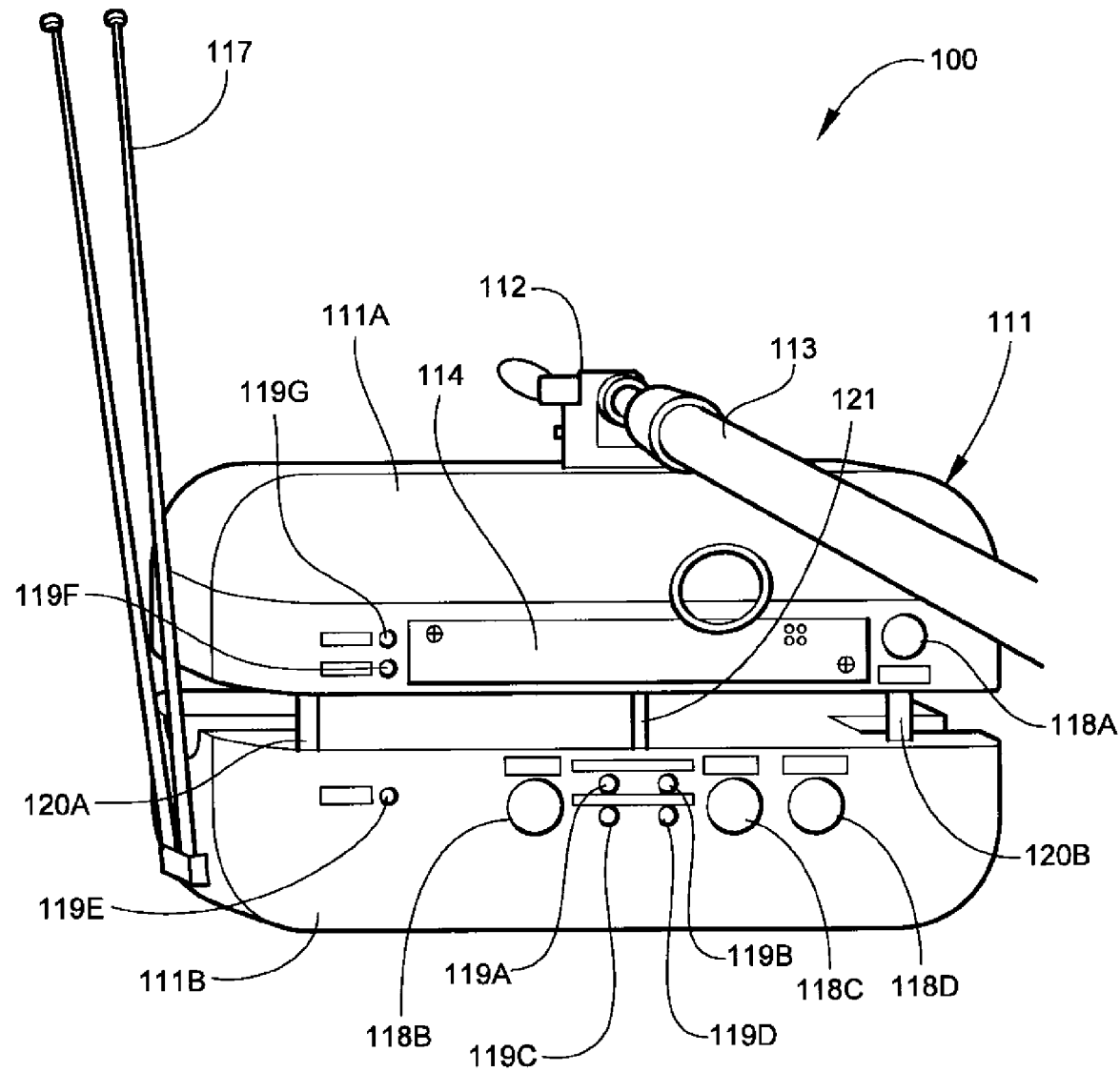
FIG. 2 is an EMAT system according to an embodiment of the invention.
Figure 3:
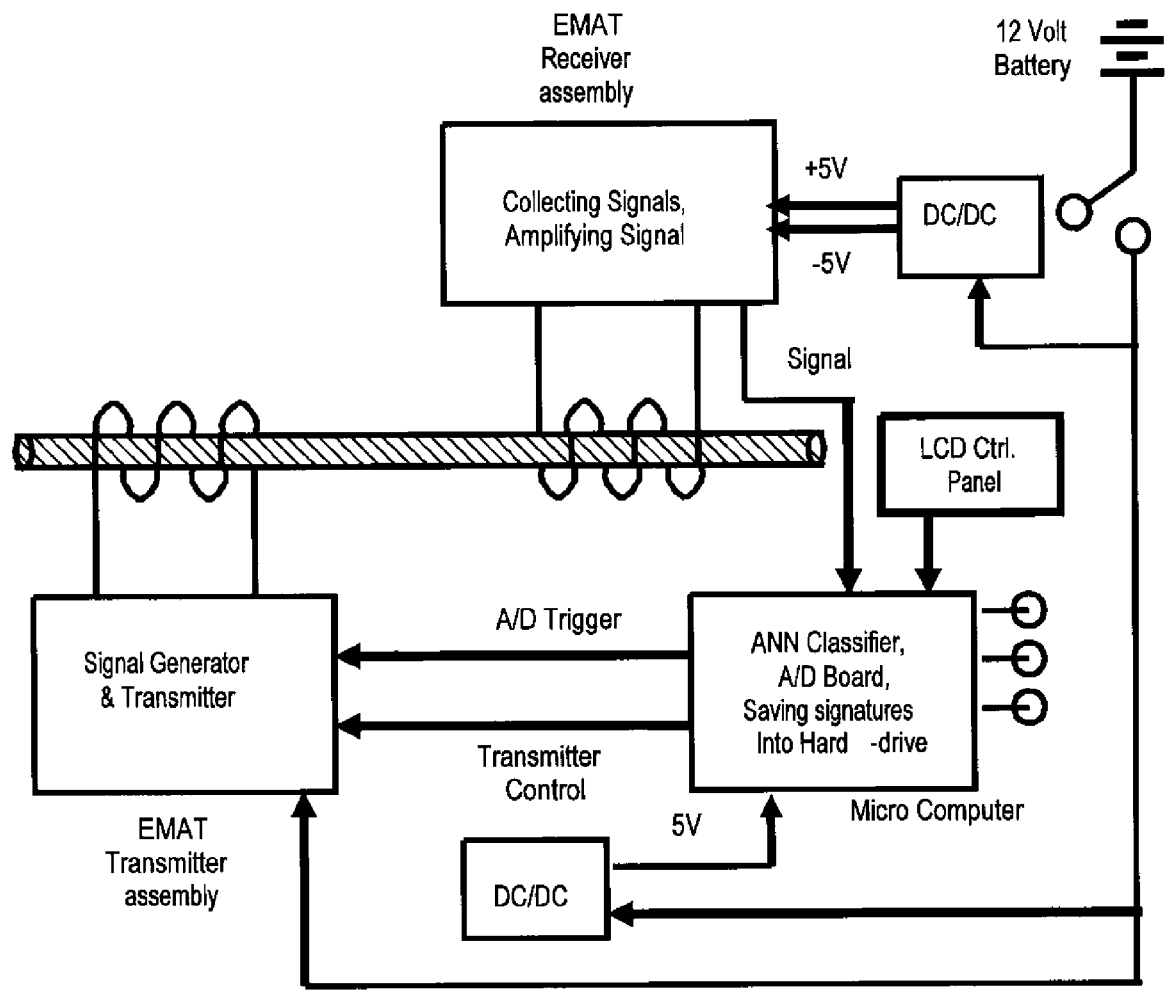
FIG. 3 is a schematic of the EMAT system of FIG. 2.

Referring to FIG. 2, an EMAT system according to an embodiment of the invention is illustrated and shown generally at reference numeral 100. The EMAT system 100 is self-contained in a housing 111 and includes transmitter and receiver units, an on-board microcontroller, wireless communication, A/D and D/A converters, a 12 volt power supply, a pulse generator, DC to DC converters, and remote command and control modules. An on-board microprocessor performs advanced mathematical analysis and uses software that includes fuzzy logic, neural network, and Adaptive Resonant Theory (ART) network for system operation, fault detection, and classification. The EMAT system 100 further includes transducers, a power amplifier, and electronics for the operation of the transducers. A schematic of the EMAT system 100 is shown in FIG. 3.

The housing 111 includes an upper housing portion 111A and a lower housing portion 111B. As illustrated, the housing 111 is a convex-shaped enclosure made of a material, such as plastic, to prevent the creation of corona, and to withstand over 500 kV and over 1000 amps. It should be appreciated that any suitable material and shape may be used for the housing 111.

The upper housing portion 111A includes an attachment device 112 for attaching a hot stick 113 to allow the EMAT system 100 to be positioned on high voltage lines. The EMAT system 100 is powered by a 12-volt battery (not shown) positioned behind a retainer plate 14 for portability. The battery is keyed to be received in a battery slot on a front of the upper housing portion 111A to prevent an incorrect battery installation.

A bounding fork 117 may be attached to a side of the lower housing portion 111B. The bounding fork 117 is used to discharge any electricity or arcs that could damage the electronics of the EMAT system 100. This is done by allowing the bounding forks 117 to make contact with a conductor prior to positioning the EMAT system 100 on the conductor and subjecting the EMAT system 100 to a high voltage.

The EMAT system 100 is operated using control switches, such as buttons 118A-118D on a front of the upper and lower housing portions 111A and 111B. The buttons 118A-118D may be operated by a remote hot stick, such as hot stick 113, and are used to perform a full conductor diagnostic and monitoring cycle. As illustrated, button 118A is the on/off switch, button 118B is the test switch, button 118C is the open switch, and button 118D is the close switch. Light emitting diodes (LEDs) 119A-119G are also positioned on the front of the upper and lower housing portions 111A and 111B to indicate the results of the diagnostic and monitoring cycle. LED 119G indicates that the power is on, LED 119F indicates that the EMAT system 100 hardware is ready, and LED 119E indicates that the EMAT system 100 is ready to perform a test. The LED's 119A-119D indicate one of four conductor conditions: normal (119A), minor abnormal (119B), major abnormal (119C), and corrosion (119D). Additionally, if the battery is fully discharged, every LED 119A-119G on the EMAT system 100 will illuminate, indicating that the EMAT system 100 is not functional.

Figure 4:
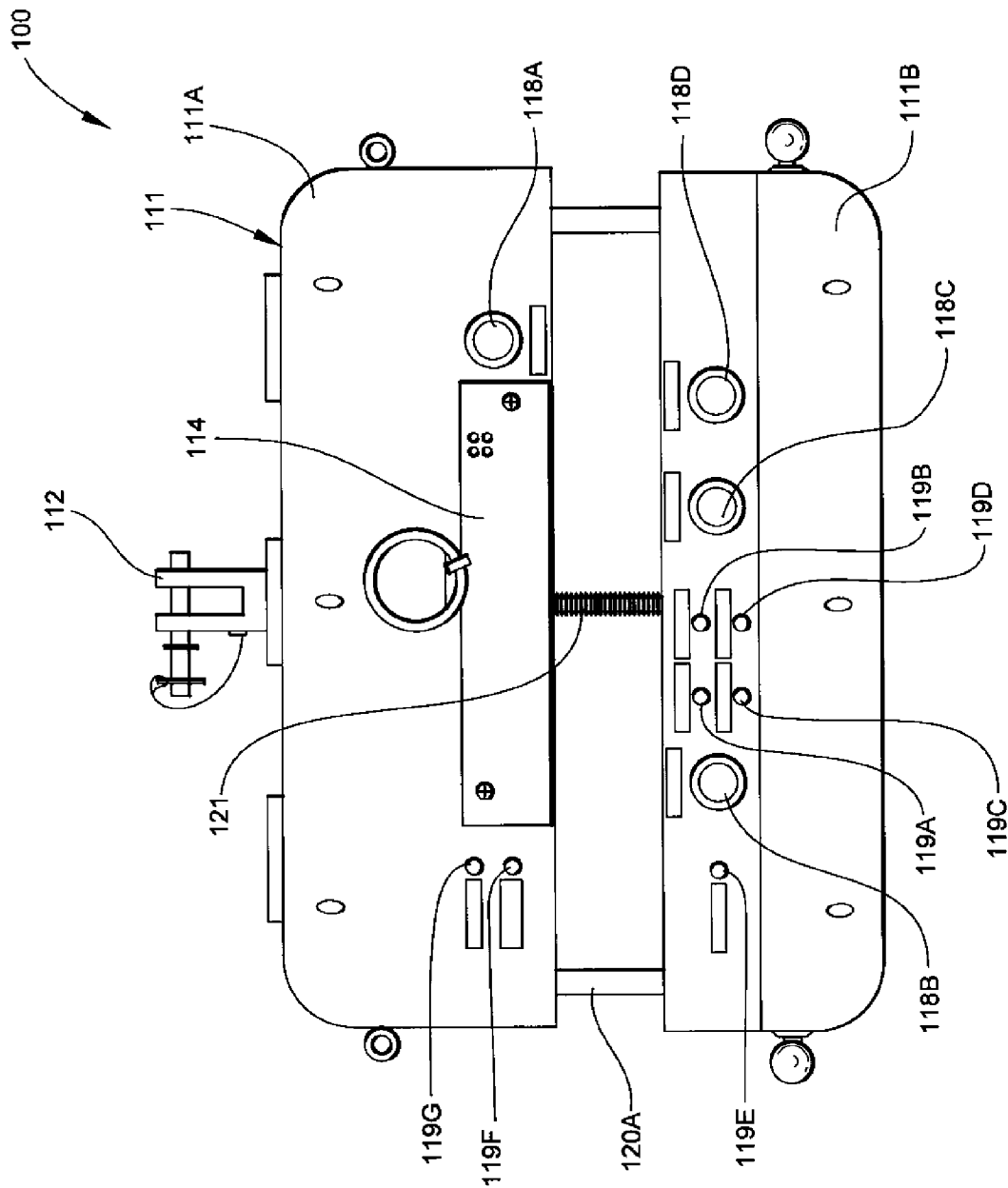
FIG. 4 is a front elevation of the EMAT system of FIG. 2 in an open position.
Figure 5:
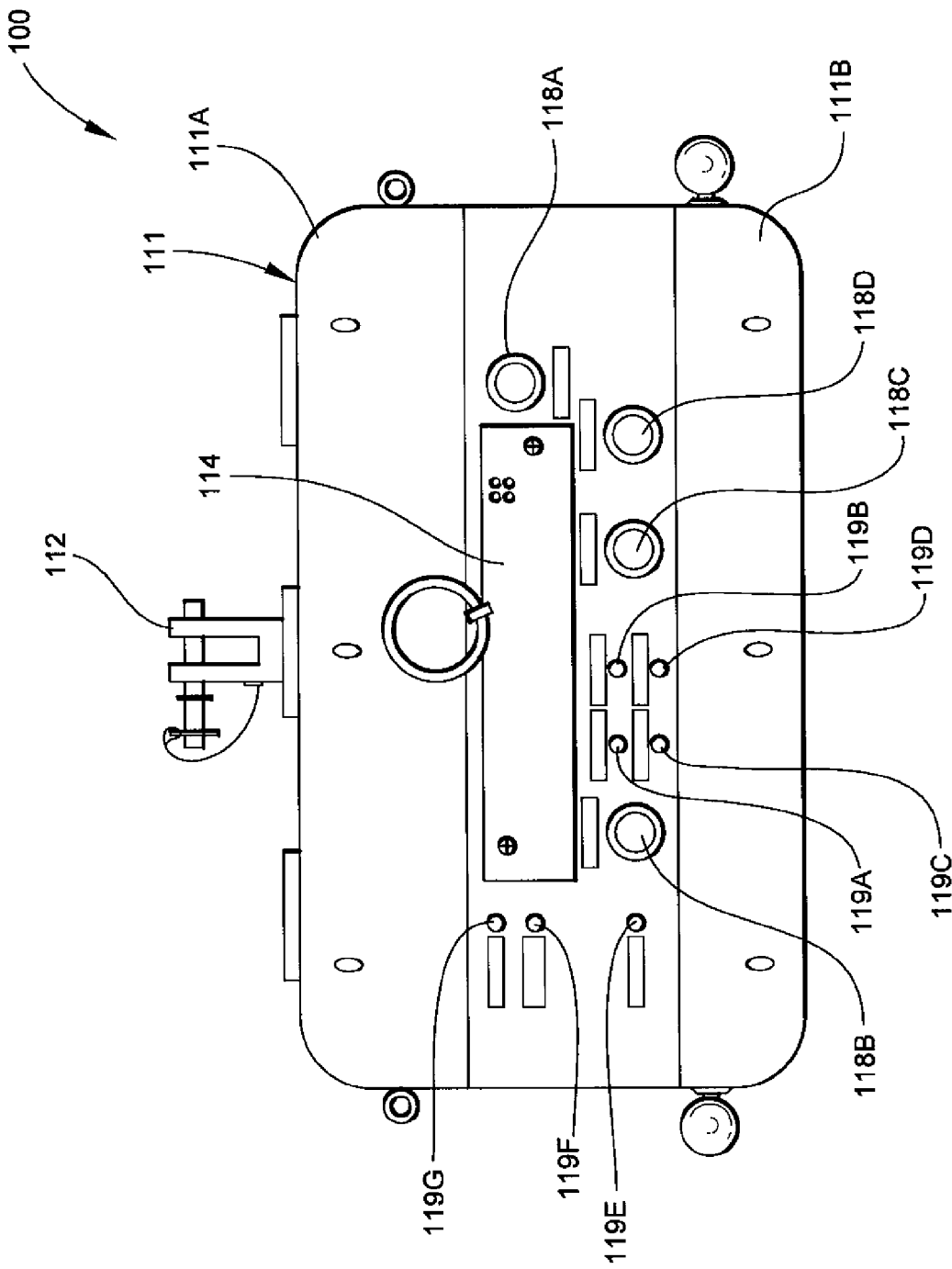
FIG. 5 is a front elevation of the EMAT system of FIG. 2 in a closed position.

The upper housing portion 111A and lower housing portion 111B are moved from an open position, FIG. 4, to a closed position, FIG. 5, around a conductor by two screw guides 120A and 120B. The screw guides 120A and 120B are operably connected to a worm gear 121 and a feedback controlled electric motor 122, shown in FIG. 17, to allow the upper and lower housing portions 111A and 111 B to be moved between the open position and the closed position remotely in the presence of high repelling forces that magnets in each of the upper housing portion 111A and lower housing portion 111B produce.

Figure 6:
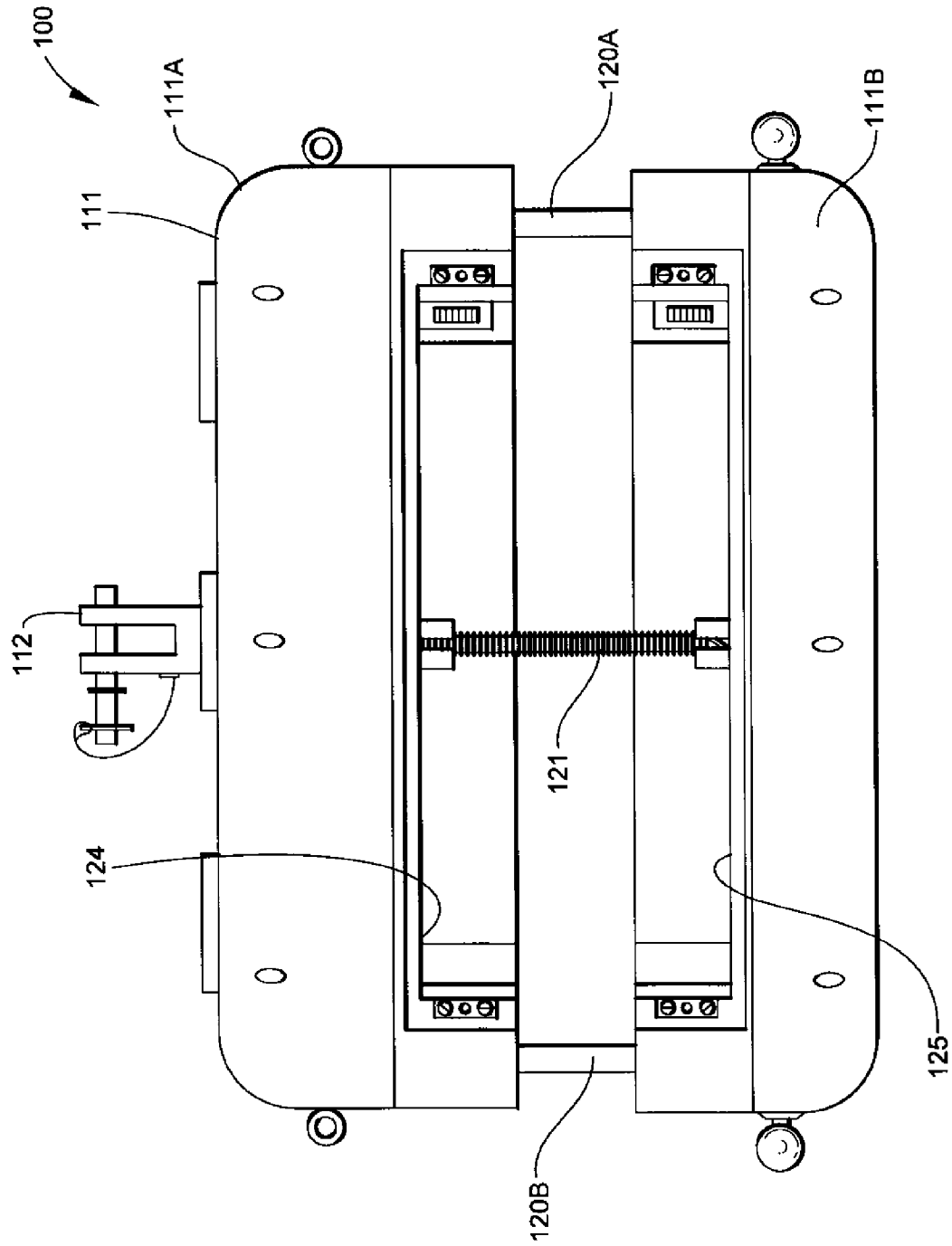
FIG. 6 is a rear elevation of the EMAT system of FIG. 2.
Figure 7:
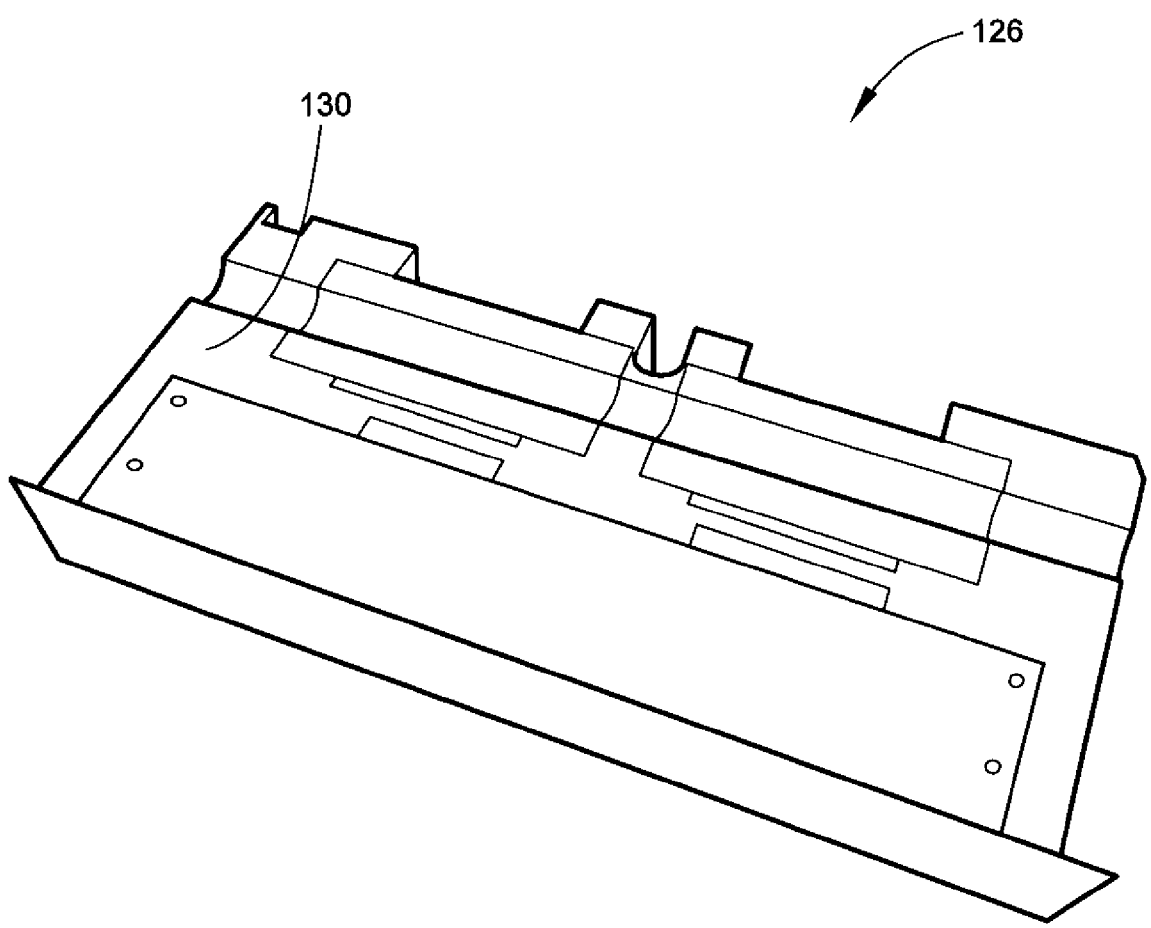
FIG. 7 is a cartridge for use in the EMAT system of FIG. 2.
Figure 8:
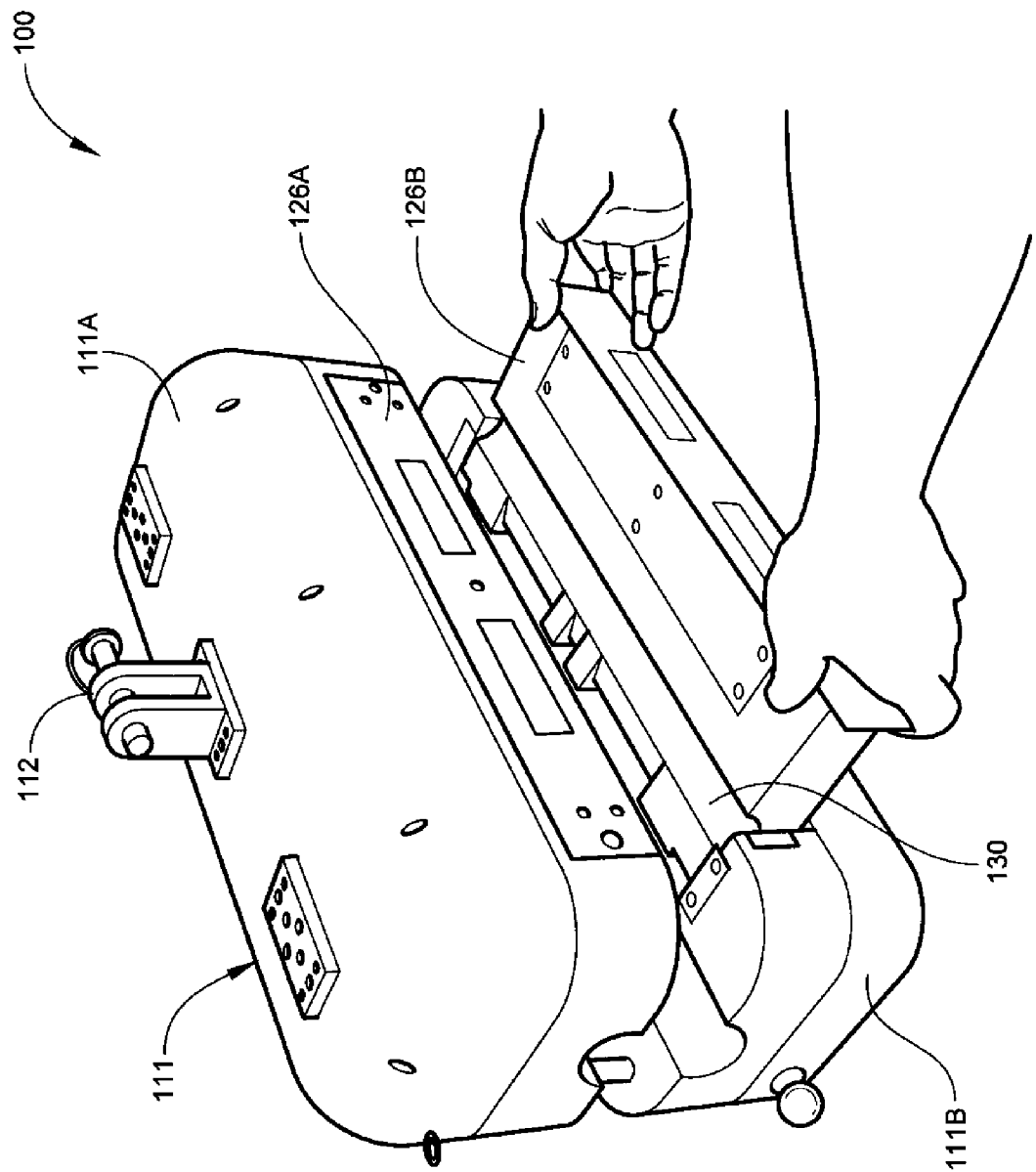
FIG. 8 shows the cartridge of FIG. 7 being installed in the EMAT system of FIG. 2.

As shown in FIG. 6, the EMAT system 100 includes a pair of recesses 124 and 125 positioned in the upper housing portion 111A and lower housing portion 111 B, respectively. Each of the recesses 124 and 125 are adapted to receive a transmitter/receiver cartridge 126, like that shown in FIG. 7. As illustrated in FIG. 8, the EMAT system 100 uses upper and lower transmitter/receiver cartridges 126A and 126B. The cartridges 126A and 126B are removable and can be interchanged with other cartridges to allow the EMAT system 100 to perform testing on conductors of various sizes. Each of the upper and lower cartridges 126A and 126B have transmitter and receiver coils. The transmitter and receiver coils of the upper and lower cartridges 126A and 126B are connected in series and function electrically as a single transmitter or receiver coil in the EMAT system 100. The cartridges 126A and 126B include a concave section 130 to allow a conductor to be received therein between the upper and lower cartridges 126A and 126B during testing.

The EMAT system 100 is used to analyze the mechanical integrity of electric power conductors. The system generates micro-scale displacement waves that are propagated through the conductor under investigation. By analyzing the conductor response to the combined torsional and longitudinal excitations, the EMAT system 100 reports the condition of the conductor.

The EMAT system 100 may be described in terms of four functional units: a transmitter, a receiver, a motor driver, and a microcontroller. Since the EMAT system needs to create electric pulses having a frequency between about 50 KHz and 200 KHz, an amplitude of between about 300 volts and 500 volts, and a current of about 30 amperes from a 12 volt battery, the transmitter includes a pulse generator circuit 131 having an H-Bridge component, a high voltage generator circuit 132, and a clocks and power on reset generator circuit 133. Example circuits for each of the generators is shown in FIGS. 9-11, and a block diagram of a programmable interval timer used in the clocks and power on reset generator circuit 133 is shown in FIG. 12.

Figure 9:
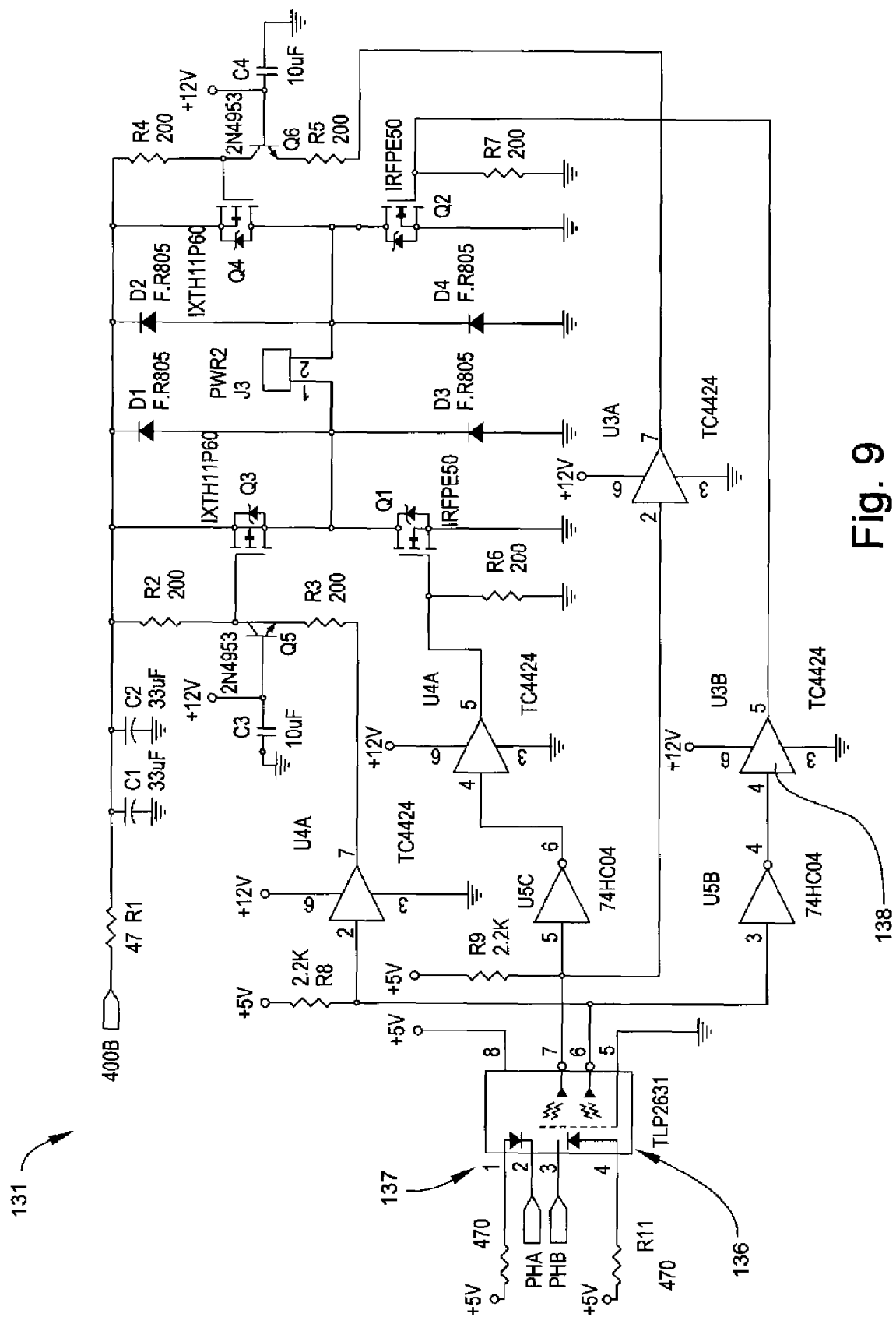
FIG. 9 shows a pulse generator circuit for a transmitter of the EMAT system of FIG. 2.
Figure 11:
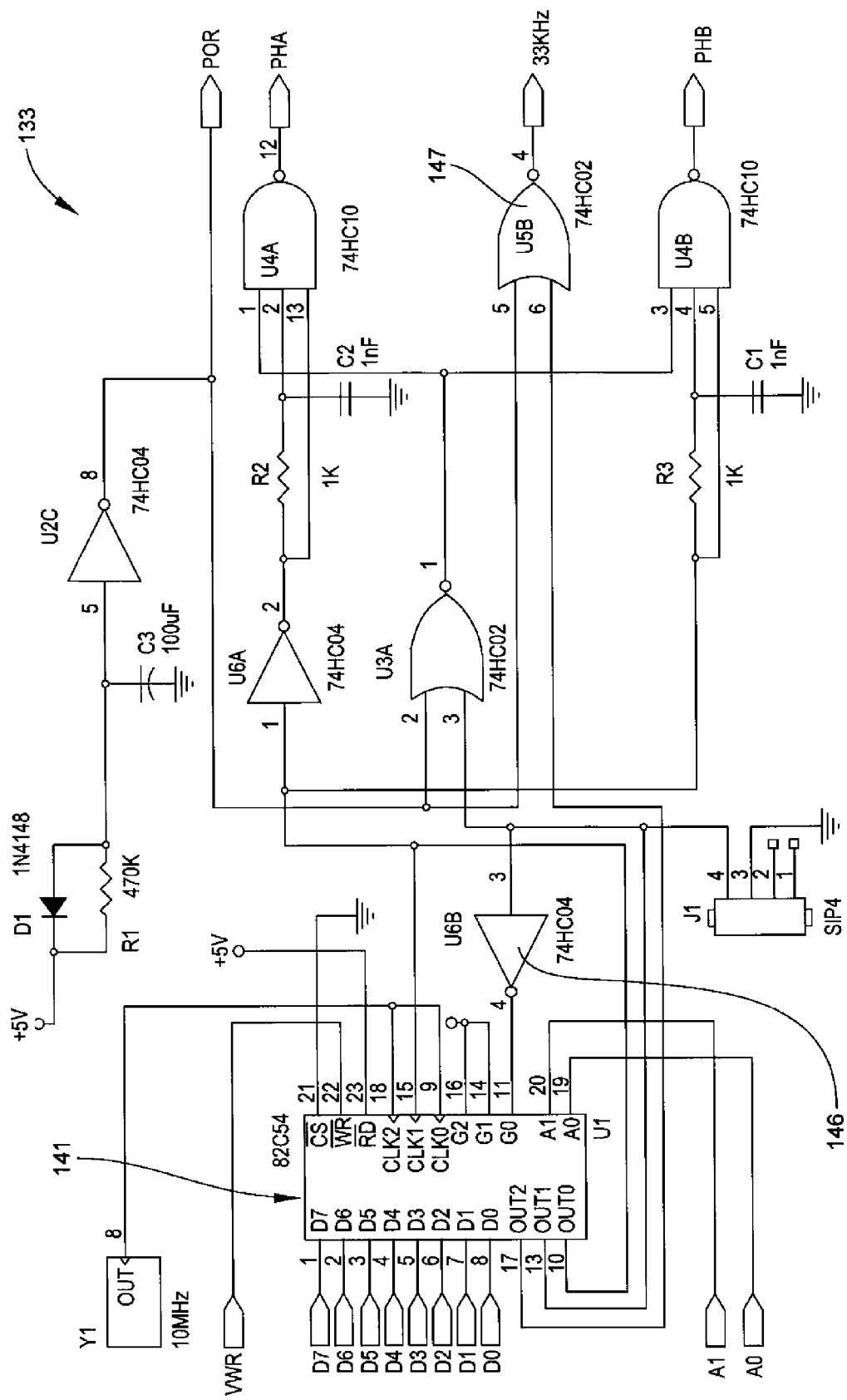
FIG. 11 shows a clocks and power on reset generator circuit for the transmitter of the EMAT system of FIG. 2.
Figure 12:
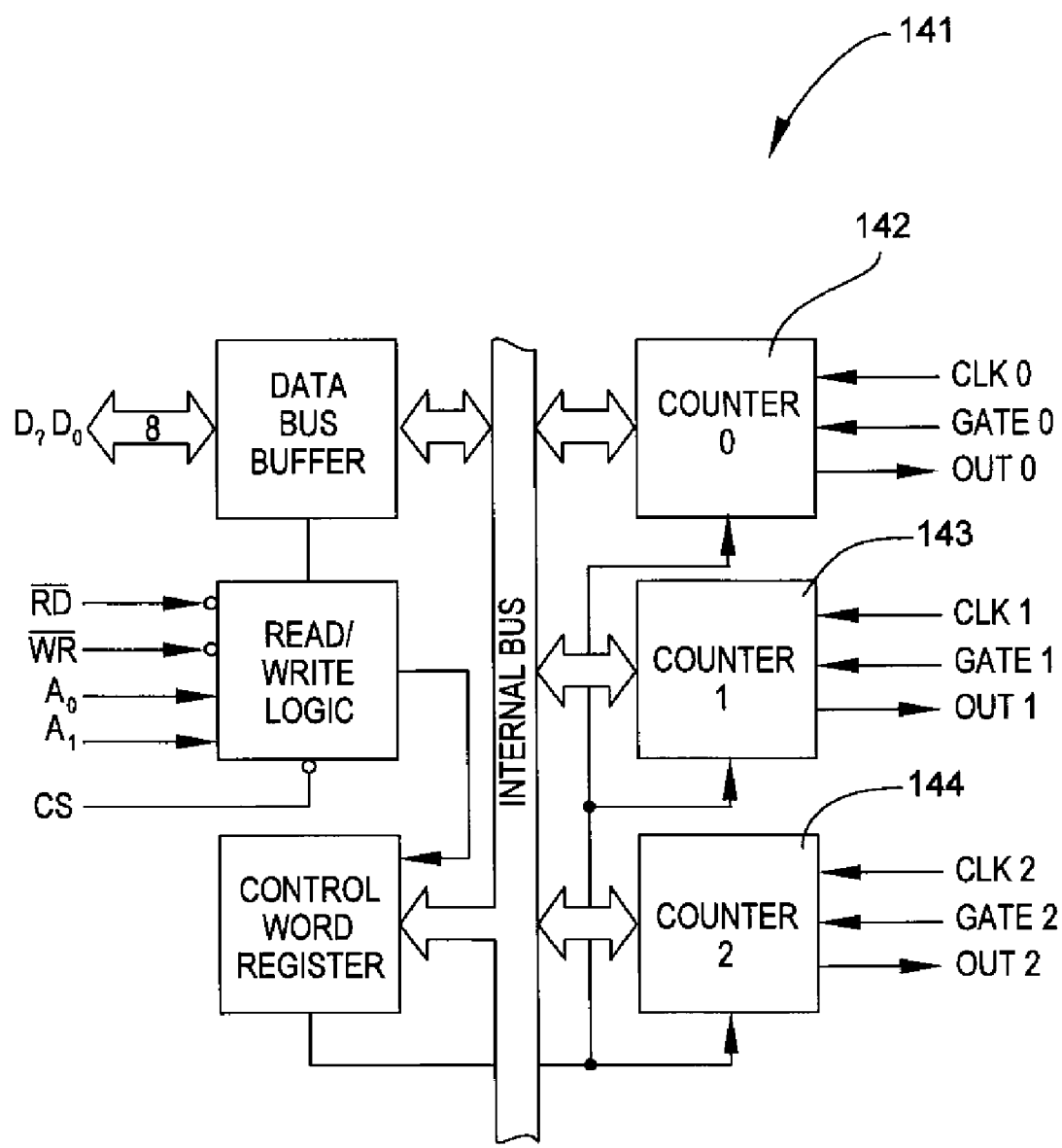
FIG. 12 is a block diagram of a programmable interval timer of clocks and power on reset generator circuit of FIG. 11.

Referring to FIG. 9, the pulse generator circuit 131 uses an opto-coupler 136, such as Toshiba's TLP2631, to create electrical isolation between a transducer drive circuitry and the clock and power on reset circuitry 133, shown in FIG. 11. An H-Bridge 137 is used to generate excitation pulses, and includes four switches that are activated to generate positive and negative pulses. PHA and PHB are alternately switched low. As a result, the output of the opto-coupler 136 goes low alternately, thus, current flows from pin 2 to pin 1 of the J3, which is connected to the transmitter coil. In the next stage PHA goes high and PHB goes low and similar operations occur in Q2 and Q3 resulting in opposite voltages being applied to the J3 pins, causing current to flow in the opposite direction In the second stage, the active component is the MOSFET gate driver IC TC4424 138. This driver 138 is capable of sinking high current (3 A) and has very low output resistances. It also shifts the signal from a Transistor Transistor Logic (TTL) compatible voltage level (+5V-0.6V) to a MOSFET gate driver voltage level (+12V).

Figure 10:
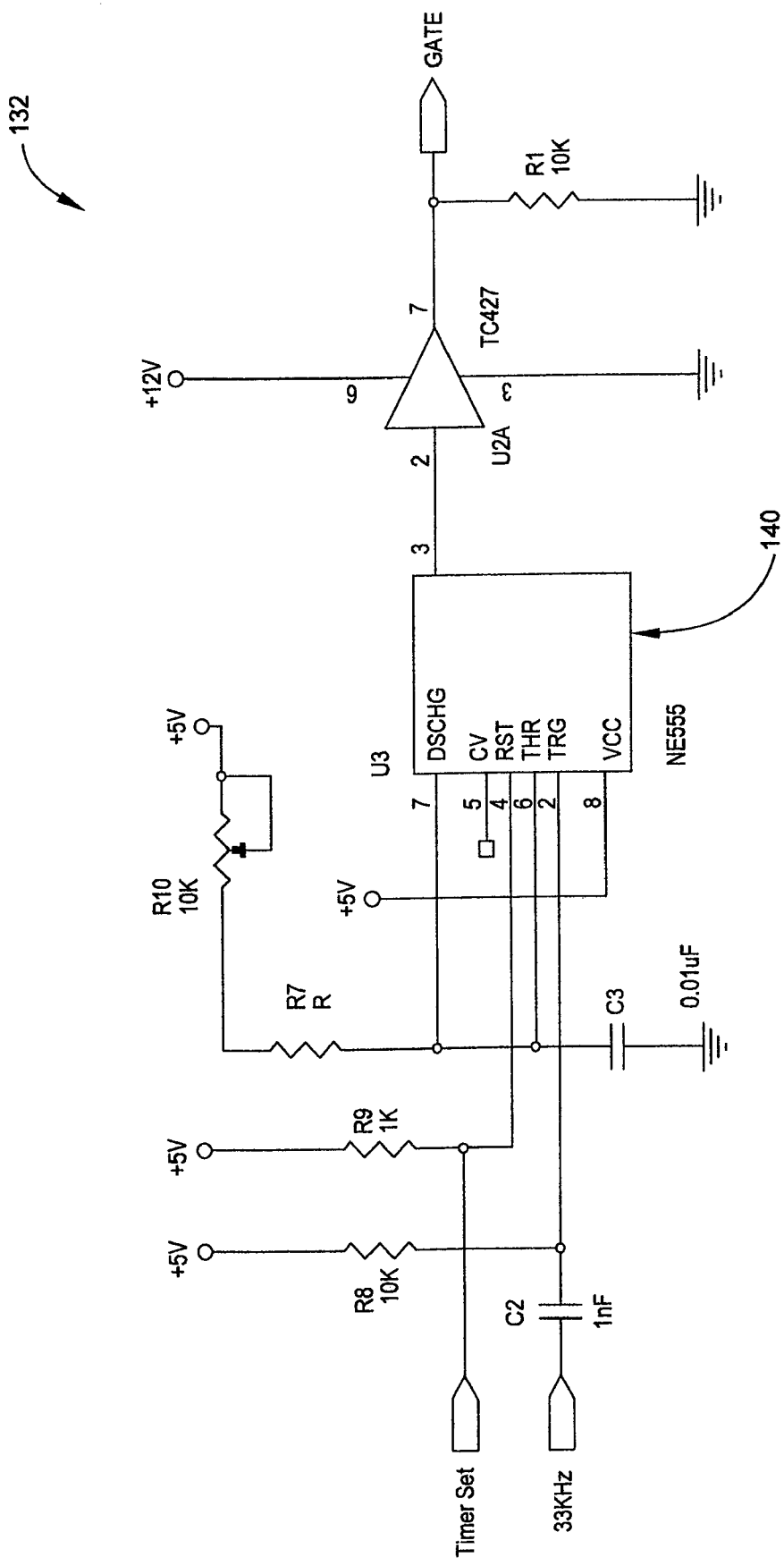
FIG. 10 shows a high voltage generator circuit for the transmitter of the EMAT system of FIG. 2.

Referring to FIG. 10, the high voltage generator circuit 132 converts 12 volt pulses to high voltage pulses, for example, 400 volts. The heart of the high voltage generator circuit 132 is the NE555 Timer IC 140. It is configured in mono-stable mode. A clock of 33 KHz is fed to the trigger input pin 2. C2 works as a DC de-coupling capacitor. (R7+R10) and C3 form the timing component. The width of the output pulse has a canonical expression: t=1.1(R×C) sec.

Referring to FIG. 11, the clocks and power on reset circuit 133 initiates the creation of pulses upon the user's command by pushing the test button 118B on the front of the EMAT system 100. The pulse generating circuit 133 also uses an on-board processor clock to assure the desired frequency of the pulse (50 KHz to 200 KHz). The central active component of this circuit is the CHMOS Programmable Interval Timer (PIT) 82C54 141.

As shown in FIG. 12, the PIT 141 has three independent 16 bit counters (blocks 142-144). Addressing inputs A1 and A0 are used to select these counters. A/RD (READ bar) signal reads from the selected counter and a INR (WRITE bar) signal writes value to the selected counter. With a fixed clock input, the counters (blocks 142-144) work as timers. On the EMAT system 100 the counters (blocks 142-144) are setup as Mode III timers. Counters 0 (block 142) and 2 (block 144) receive a 10 MHz clock signal from a crystal oscillator. Depending on the microcontroller, counter 0 (block 142) is set-up to generate corresponding frequencies. Counter 1 (block 143) generates a delay between successive pulse bursts.

An output low on counter 1 (block 143) sets gate 0 high and vice versa, because of inverter U6B 146 between them. Also the output of counter 1 (block 143) controls activation of PHA and PHB outputs when there is a low on POR. The NOR gate U5B (74HC02) 147 ensures that there is no 33 KHz pulse going out of this circuit when the POR is high.

Figure 13:
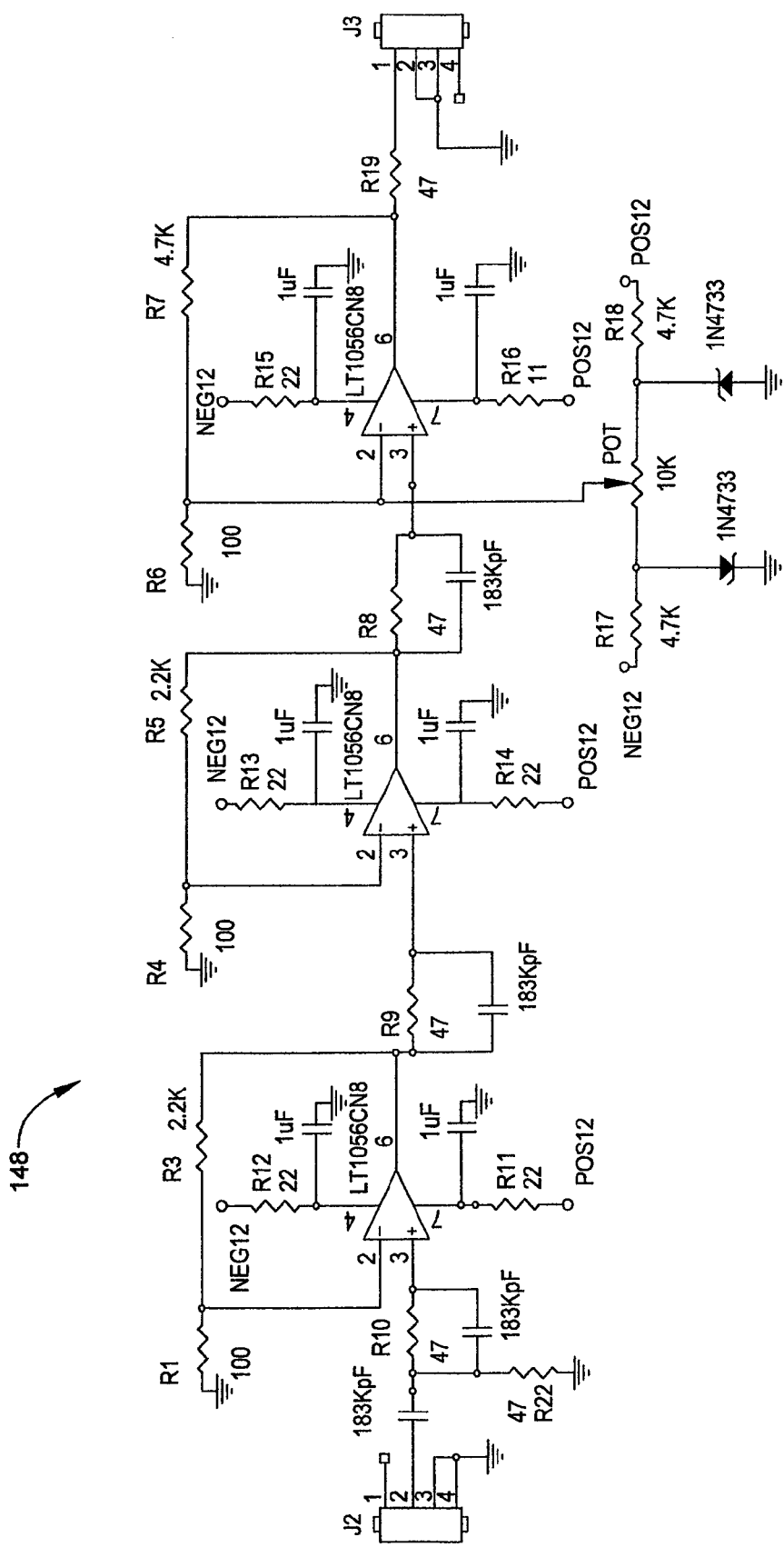
FIG. 13 shows a signal amplifier circuit for a receiver of the EMAT system of FIG. 2.
Figure 14:
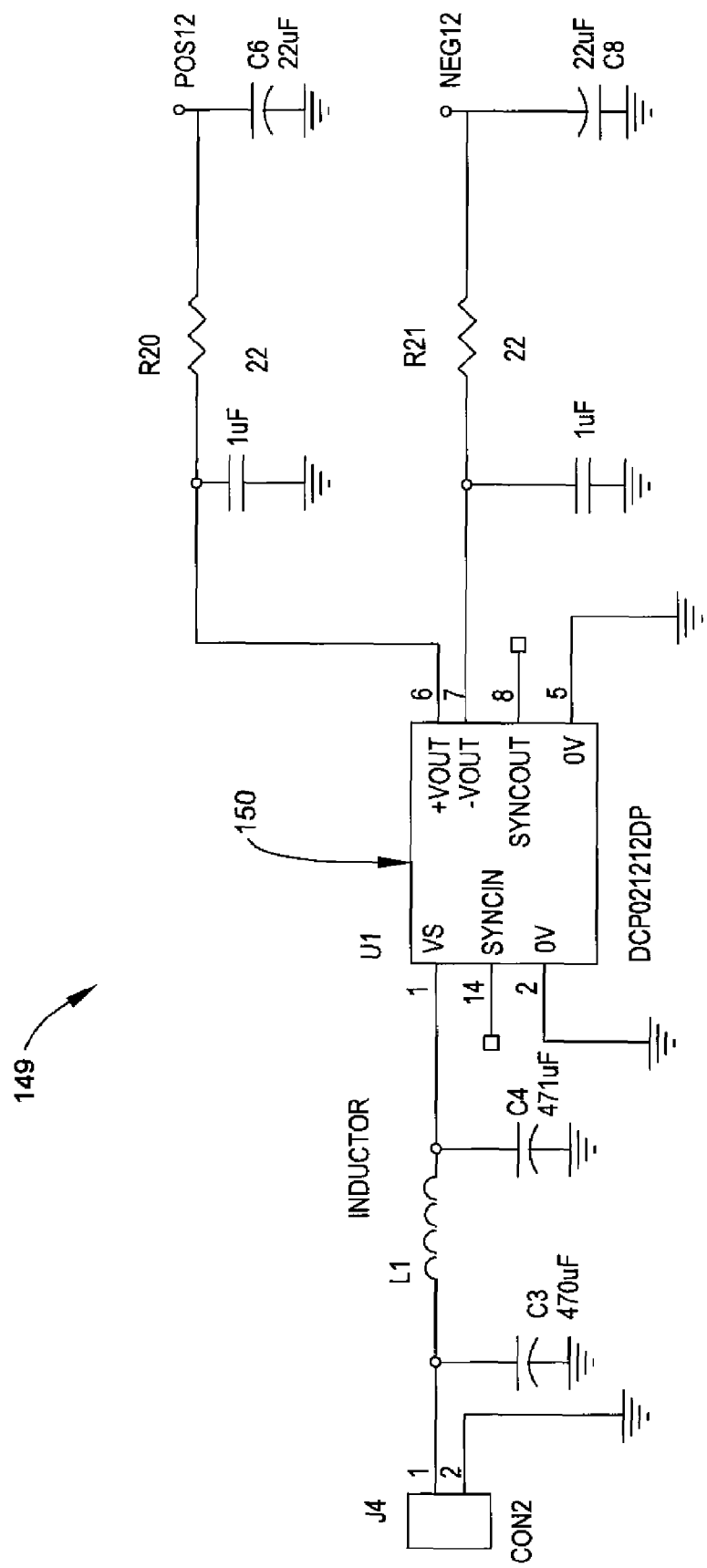
FIG. 14 shows a negative voltage generator circuit for the receiver of the EMAT system of FIG. 2.

Referring to FIGS. 13 and 14, the receiver includes a signal amplifier 148, FIG. 13, and a negative voltage generator 149, FIG. 14. Signatures from a conductor will be in the form of current induced by the reflective displacement waves of the conductor and the magnetic field of the receiver. This signature needs to be conditioned and amplified, and to represent both a positive and a negative range of these signatures.

As shown in FIG. 13, J2 is the input from the receiver coil. The voltage induced in the receiver coil appears here. The following capacitor 183 KpF is being used to block any DC components of the input. Because this circuit is concerned with the signal variability only, it does not count on the DC level.

As shown in FIG. 14, the active element of the negative voltage generator circuit 149 is the DCP021212DP 150. This is an unregulated DC/DC converter. This provides negative voltage on pin 7 and a positive voltage on pin 6. The external capacitors connected to these two pins serve to stabilize the output voltage and hence eliminate noise.

Figure 15:
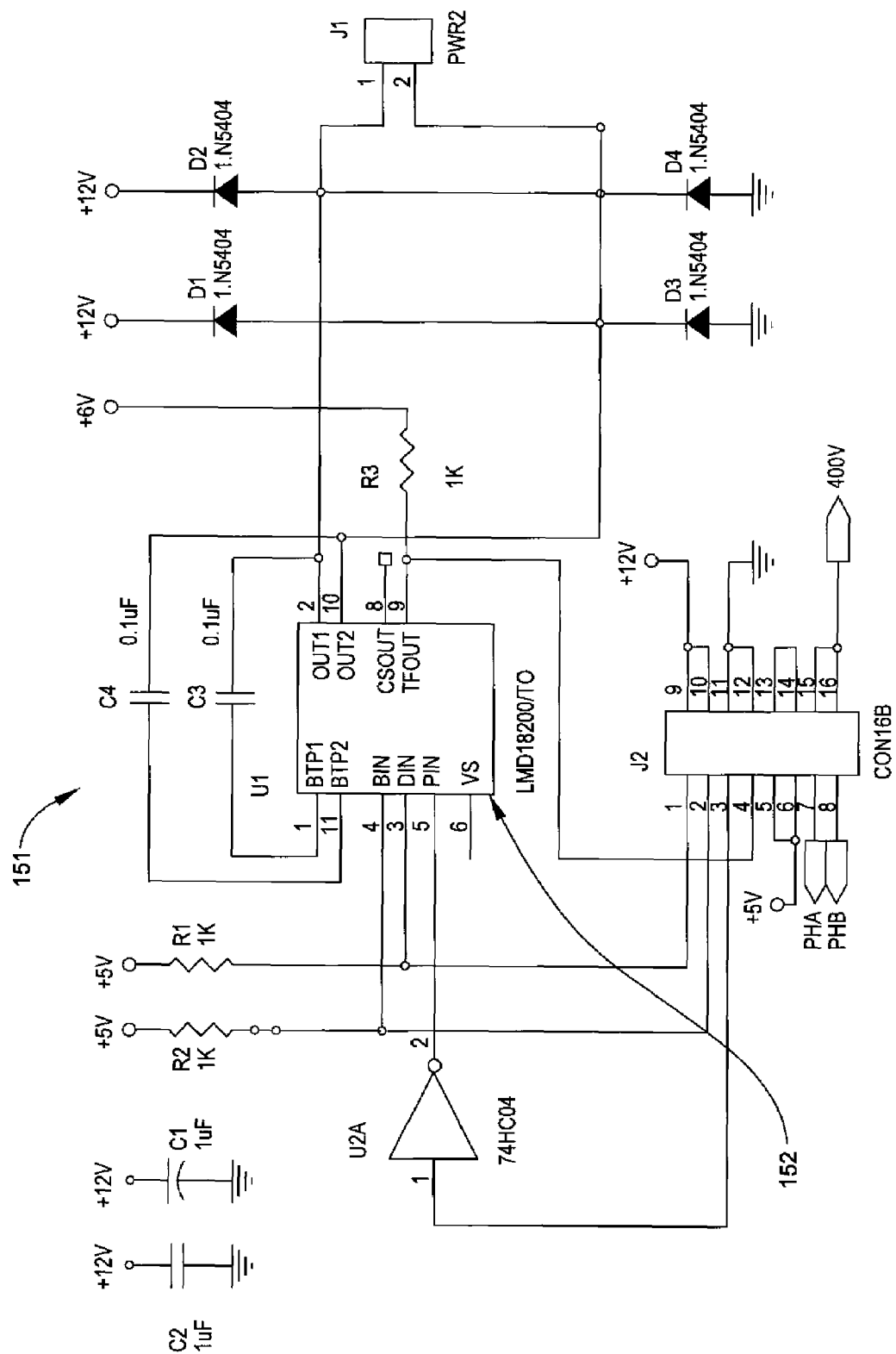
FIG. 15 shows a motor driver circuit for the EMAT system of FIG. 2.

Referring to FIG. 15, a motor driver circuit 151 uses an LMD18200/T0 chip 152. It is an H-bridge for controlling the DC motor 122, shown in FIG. 17, by changing supply voltage polarity and turning the motor 122 on and off. The DC motor 122 is used to open and close the EMAT system 100. The motor 122 is operated off of the EMAT system 100 12-volt battery. Since it has to rotate both clockwise and counter-clockwise to open and close the EMAT system 100, its polarity needs to be switched. Also, it uses an optical feedback sensor to prevent over-closing or over-opening the EMAT system 100, thus damaging the EMAT system 100.

Figure 16:
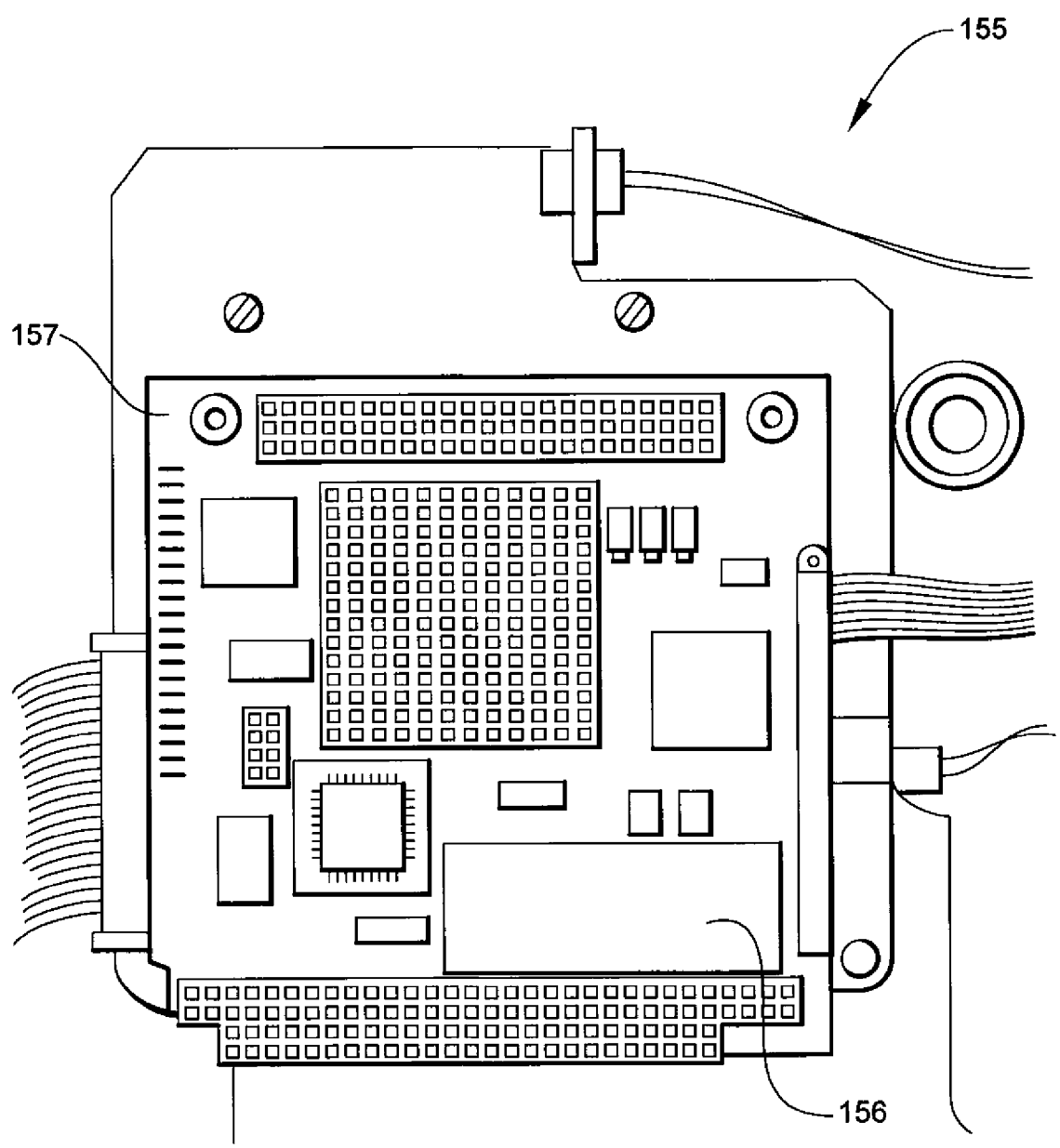
FIG. 16 shows an embedded processor of the EMAT system of FIG. 2.

Referring to FIG. 16, the EMAT system 100 uses a microcontroller 155 that is centered on the VersaLogic Corporation's Bobcat PC/104 module 156. The Bobcat module 156 also contains integrated peripheral connections such as a serial port utilized by the EMAT system 100. Attached to the Bobcat 156 is a PC/104 compatible Chase Scientific CS-210 Data Acquisition (DAQ) card 157. The DAQ card 157 utilizes a 12-bit Analog to Digital Converter (A/D) to provide the digital data to the EMAT system 100. It should be appreciated that any suitable DAQ card or PC/104 module may be used.

Figure 17:
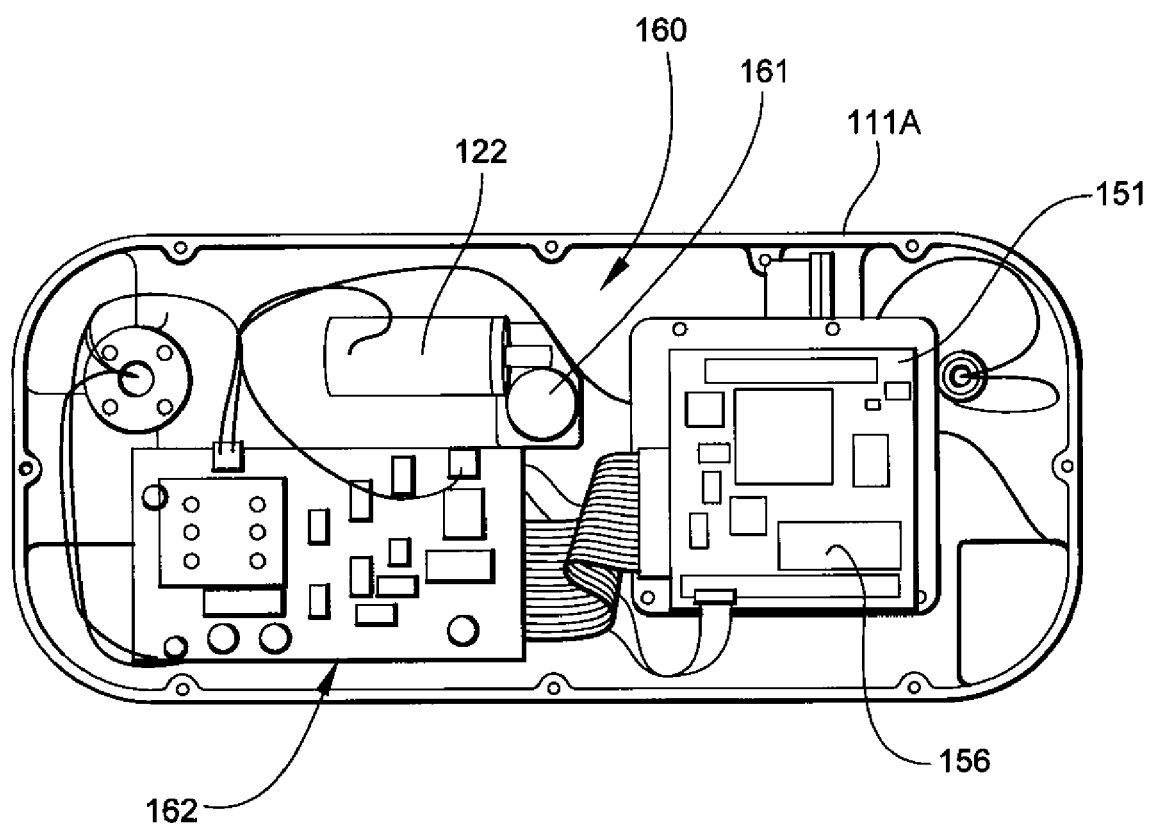
FIG. 17 shows the embedded processor of FIG. 16, a motor drive assembly, and the motor drive circuit of FIG. 15 positioned in an upper housing portion of the EMAT system of FIG. 2.
Figure 18:
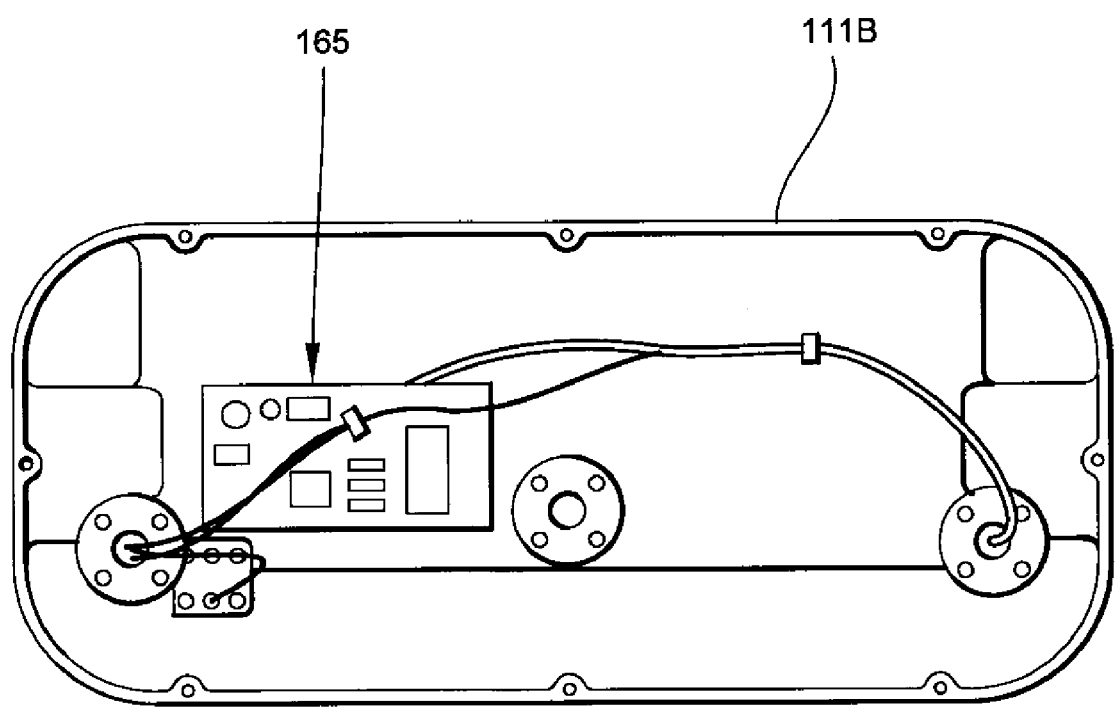
FIG. 18 shows the signal amplifier of FIG. 13 positioned in a lower housing portion of the EMAT system of FIG. 2.

As shown in FIG. 17, the majority of the EMAT system 100 electronics are housed in the upper housing portion 111A. The Bobcat processor module 156 and Chase Scientific DAQ card 157 can be seen in a stacked orientation on the right side of this figure. A motor drive assembly 160 that includes the motor 122 and a gear drive 161 are located near the center of the upper housing portion 111A. Other motor drive electronics/high voltage coil driver electronics 162 can be seen on the left side of this figure. As shown in FIG. 18, the lower housing portion 111 B of the EMAT system 100 houses the receiver amplifier 165.

The EMAT system 100 does not require an operator to have any special skills to operate the EMAT system 100. Instead, the EMAT system 100 includes built in intelligence to perform feature extraction and signature analysis using nonlinear signal processing. Thus, the EMAT system 100 can provide an operator with an indication of the extent of damage in the conductor by using its intelligent built in software and highly specialized filters and algorithms to quickly and accurately detect corrosion, poorly installed splices, broken strands in the conductor, loss of cross-section in anchor rods, and ground melt risers.

The EMAT system 100 is used by placing the EMAT system 100 on an electric power conductor. This is done using the hot-stick 113, as shown in FIG. 2. The hot-stick 113 is made from insulating fiberglass, and is necessary to insulate a user from the energized high voltage power line.

Figure 19:
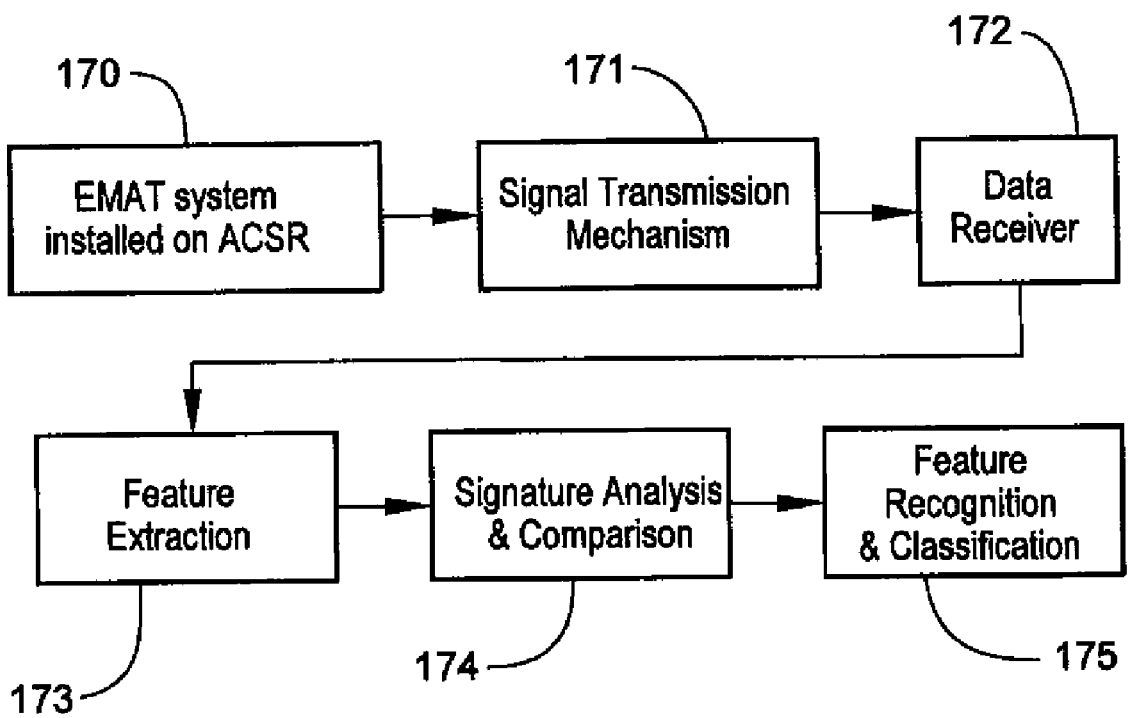
FIG. 19 is a block diagram of a fault diagnostics procedure for the EMAT system of FIG. 2.

As shown in FIG. 19, once the EMAT system 100 has been installed on the conductor (block 170), an amplified signal is transmitted to the conductor by the transmitter (block 171) and then received by the receiver (block 172). The amplified signal is stored in the memory of the microcomputer and is processed through an artificial neural network (blocks 173-175). Artificial neural networks have been applied widely for pattern recognition problems. The most popular one is a Multilayer Perceptron (MLP) classifier based on the back-propagation learning rule (BP algorithm). Since the main issue in classification is robustness to variances of general test sets, an Adaptive Resonant Theory (ART) neural network for the classification has been used.

The ART neural network (blocks 173-175) resolves the instability of feedforward instar-outstar systems. The ART neural network (blocks 173-175) is not only stable enough for significant past learning, but also adaptable enough to incorporate new information whenever it may appear. The ART neural network (blocks 173-175) is composed of three layers, and in the first layer, the preprocessing for the other layers is accomplished. Usually, the input pattern preprocessing includes noise reduction, contrast enhancement, normalization, and input transformation.

The EMAT transmitter generates pulses and impinges them onto the conductor through transmitting coils. The EMAT receiver captures the reflected signals and amplifies them. The raw data is acquired at a very high sampling frequency. An eight step advanced signal processing and filtering process is used. This is done by obtaining ASCII coded frequency sweep data files, making data sets mean zeroed, applying a high order band-pass filter, overlapping data files on a time domain, extracting the maximum value from each band-pass filtered data and constructing one time domain data file, strategically removing the initial points and final data points, applying a running average filter, and re-sampling of the data. A low-pass filter is applied to reduce the noise influence.

After analysis an overall damage rating is given, which quantifies the amount of damage that a given conductor has sustained. The information on the EMAT system 100 operation and the result of diagnostics after a classification process are displayed by turning on different LEDs on the front of the EMAT system 100.

A self-contained apparatus for inspection of energized and de-energized electric conductors is described above. Various details of the invention may be changed without departing from its scope. Furthermore, the foregoing description of the preferred embodiments of the invention and best mode for practicing the invention are provided for the purpose of illustration only and not for the purpose of limitation.

I claim:

1. An apparatus for inspecting electrical conductors, comprising:
    (a) a housing;
    (b) at least one transmitter contained within the housing for generating and impinging pulses onto an electrical conductor, such that the pulses travel through and are reflected by the electrical conductor;
    (c) at least one receiver contained within the housing and adapted to receive reflected pulses from the electrical conductor, the receiver having a negative voltage generator to stabilize an output voltage and reduce noise;
    (d) a controller for determining a condition of the electrical conductor based on an evaluation of the reflected pulses; and
    (e) at least one indicator for displaying the condition of the electrical conductor determined by the controller.

2. The apparatus according to claim 1, wherein the housing includes an upper housing portion and a lower housing portion.

3. The apparatus according to claim 2, wherein the upper housing portion and lower housing portion are moveable relative to each other from an open position for receiving the electrical conductor to a closed position for inspecting the electrical conductor.

4. The apparatus according to claim 3, and further including a motor drive assembly for moving the upper housing portion and lower housing portion relative to each other from the open position to the closed position, the motor drive assembly including:
    (a) a feedback controlled motor; and
    (b) a gear drive.

5. The system according to claim 4, and further including a motor driver for controlling the motor drive assembly.

6. The apparatus according to claim 4, and further including screw guides operably connected to the gear drive and feedback controlled motor to allow the upper housing portion and lower housing portion to be moved from the open position to the closed position.

7. The apparatus according to claim 2, wherein the upper housing portion and lower housing portion each include a recess for receiving a transmitter/receiver cartridge therein.

8. The apparatus according to claim 7, wherein each of the transmitter/receiver cartridges is operably connected to the at least one transmitter and the at least one receiver.

9. The apparatus according to claim 7, wherein each of the transmitter/receiver cartridges is removable and can be interchanged with other transmitter/receiver cartridges for testing on various sized electrical conductors.

10. The apparatus according to claim 7, wherein each of the transmitter/receiver cartridges include both a transmitter coil and a receiver coil.

11. The apparatus according to claim 10, wherein the transmitter coil and receiver coil for each of the transmitter/receiver cartridges are connected in series.

12. The apparatus according to claim 1, wherein the at least one transmitter and at least one receiver form an electromagnetic acoustic transducer system.

13. The apparatus according to claim 1, wherein the controller includes an on-board microprocessor for evaluating the condition of the electrical conductor.

14. The apparatus according to claim 13, wherein the microprocessor uses software selected from the group consisting of fuzzy logic, neural network, and adaptive resonant theory network to provide system operation, fault detection, and classification of the condition of the electrical conductor.

15. The apparatus according to claim 1, wherein the housing includes an attachment device for attaching a hot stick thereto to allow the apparatus to be positioned on energized electrical conductors.

16. The apparatus according to claim 1, wherein a bounding fork is connected to the housing to discharge any electrical charge that could damage the apparatus when placing the apparatus on an energized electrical conductor.

17. The apparatus according to claim 1, wherein the housing is curve-shaped to prevent corona and made of a material capable of withstanding at least 500 kV and at least 1000 amperes.

18. The apparatus according to claim 1, and further including a plurality of switches positioned on the housing for manually controlling the apparatus.

19. The apparatus according to claim 1, wherein the at least one transmitter includes a pulse generator for creating electric pulses having a frequency between about 50 KHz and about 200 KHz.

20. The apparatus according to claim 1, wherein the at least one transmitter includes a voltage generator for creating electric pulses of a pre-defined voltage.

21. The apparatus according to claim 1, wherein the at least one transmitter includes a clocks and power on reset generator for initiating the creation of pulses in response to actuation of a test switch positioned on the housing.

22. The apparatus according to claim 1, wherein the at least one receiver includes a signal amplifier for amplifying current induced by reflective displacement waves of the conductor.

23. A self-contained electromagnetic acoustic transducer system for inspecting energized and de-energized electrical conductors, comprising:
    (a) a first transmitter/receiver cartridge releasably secured in a recess of an upper housing portion of a housing and a second transmitter/receiver cartridge releasably secured in a recess of a lower housing portion of the housing, the upper housing portion and lower housing portion being operably attached to each other for movement between an open position for receiving an electrical conductor between the first and second transmitter/receiver cartridges and a closed position where the electrical conductor is clamped between the first and second transmitter/receiver cartridges for testing;
    (b) at least one transmitter operably connected to the first and second transmitter/receiver cartridges for generating and impinging pulses onto the electrical conductor, wherein the pulses travel through and are reflected by the electrical conductor;
    (c) at least one receiver operably connected to the first and second transmitter/receiver cartridges for receiving reflected pulses from the electrical conductor;

(d) a controller for determining a condition of the electrical conductor based on an evaluation of the reflected pulses; and (e) a plurality of indicators for displaying the condition of the electrical conductor determined by the controller.

24. The system according to claim 23, wherein the first and second transmitter/receiver cartridges are removable and can be interchanged with other transmitter/receiver cartridges for testing on various sized electrical conductors.

25. The system according to claim 23, wherein the first and second transmitter/receiver cartridges each include a transmitter coil and a receiver coil.

26. The system according to claim 25, wherein the transmitter coil and receiver coil for each of the first and second transmitter/receiver cartridges are connected in series and appear as a single transmitter coil or receiver coil to the system.

27. The system according to claim 23, wherein the at least one transmitter includes:

(a) a pulse generator for creating electric pulses having a frequency between about 50 KHz and about 200 KHz;

(b) a high voltage generator for creating high voltage electric pulses; and (c) a clocks and power on reset generator for initiating the creation of pulses in response to actuation of a test switch.

28. The system according to claim 23, wherein the at least one receiver includes:

(a) a signal amplifier for amplifying current induced by reflective displacement waves of the conductor; and (b) a negative voltage generator to stabilize an output voltage and reduce noise.

29. A method for inspecting an electrical conductor, comprising the steps of:

(a) providing an apparatus having:
   (i) an upper housing portion movably connected to a lower housing portion, the upper and lower housing portions having recesses adapted to receive transmitter/receiver cartridges therein;
   (ii) at least one transmitter;
   (iii) at least one receiver; and
   (iv) at least one controller;

(b) placing the apparatus on an electrical conductor such that the electrical conductor is positioned between the upper housing portion and the lower housing portion;

(c) transmitting a signal through the electrical conductor using the at least one transmitter;

(d) capturing a reflection of the signal with the at least one receiver;

(e) processing and filtering the reflection of the signal in the controller; and (f) providing an indication of a condition of the electrical conductor based on the processed and filtered reflection of the signal.

30. The method according to claim 29, and further including the step of attaching a hot stick to an attachment device on the upper housing portion.

31. The method according to claim 29, and further including the step of positioning a first transmitter/receiver cartridge in a recess of the upper housing portion and a second transmitter/receiver cartridge in a recess of the lower housing portion, wherein the first and second transmitter/receiver cartridges are sized for the electrical conductor.

32. The method according to claim 29, and further including the step of moving the upper housing portion and lower housing portion to an open position for receiving the electrical conductor.

33. The method according to claim 31, and further including the step of moving the upper housing portion and lower housing portion to a closed position for clamping the electrical conductor between the first and second transmitter/receiver cartridges.

34. The method according to claim 29, wherein the step of processing and filtering the reflection of the amplified signal includes the steps of:

(a) obtaining ASCII coded frequency sweep data files;
(b) making data sets mean zeroed;
(c) applying a high order band-pass filter;
(d) overlapping data files on a time domain;
(e) extracting the maximum value from each band-pass filtered data and constructing one time domain data file;
(f) removing the initial data points and final data points;
(g) applying a running average filter; and
(h) re-sampling of data.

* * * * *